Nov. 16, 1954 E. S. BOERNER Plant Pat. 1,319
ROSE PLANT
Filed Oct. 20, 1953
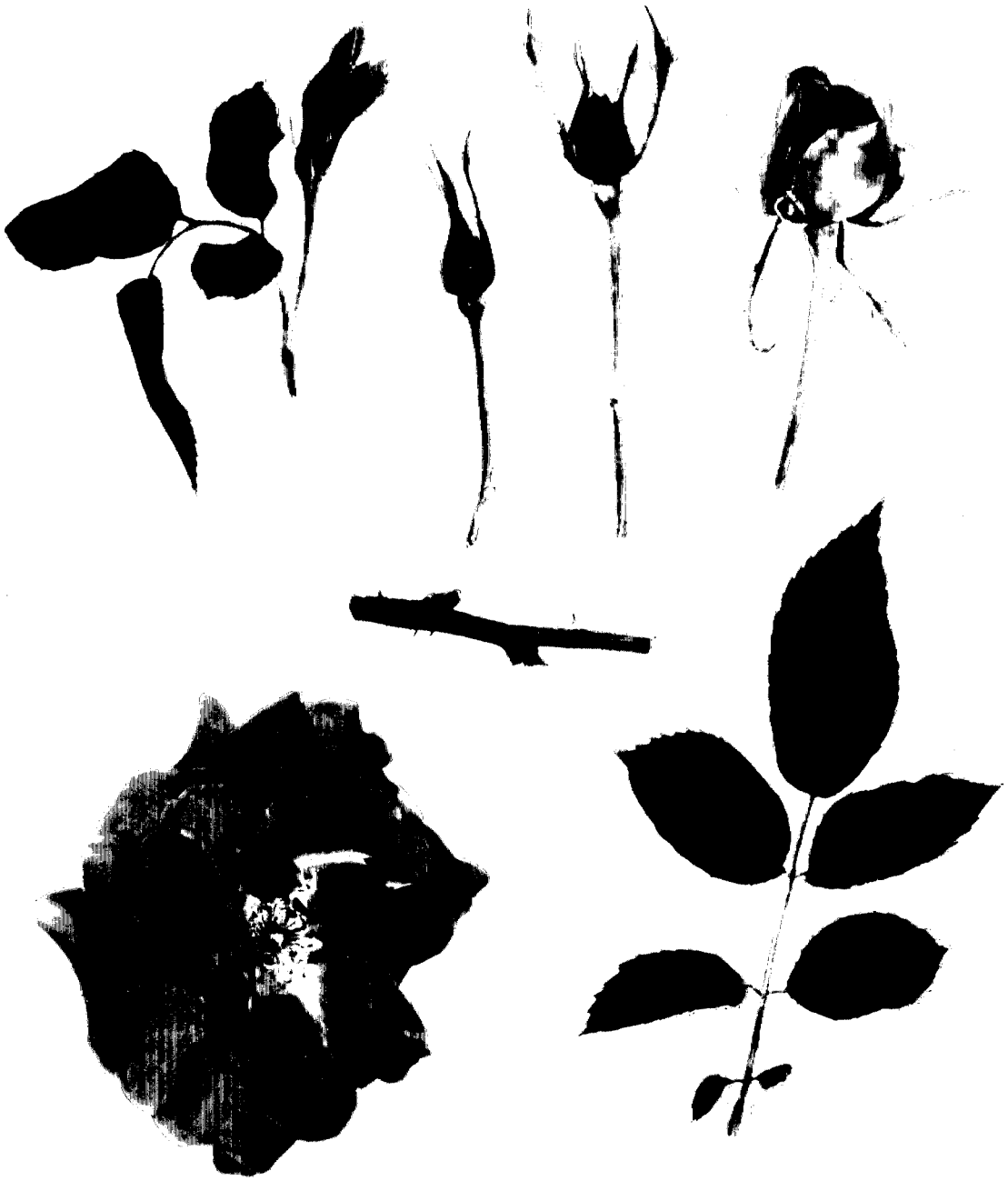
Inventor.
E. S. Boerner
By: Robb & Robb
Attorneys.

United States Patent Office

Plant Pat. 1,319

Patented Nov. 16, 1954

1,319

ROSE PLANT

Eugene S. Boerner, Newark, N. Y., assignor to Jackson & Perkins Company, Newark, N. Y., a corporation of New York Application October 20, 1953, Serial No. 387,339

1 Claim. (Cl. 47—61)

The present invention relates to a new and distinct variety of rose plant of the large-flowered polyantha class, which was originated by me by crossing the variety "Chatter" (Plant Patent No. 739) with the variety "Red Pinocchio" (Plant Patent No. 812).

The primary objective in making this cross was to improve certain of the characteristics of the parent varieties, as by combining the best qualities of each, and more particularly, to improve the form and shape of the flowers of the variety "Chatter." This objective was fully achieved, as evidenced by the fact that the new variety produces buds of relatively larger size than those of the parent variety "Chatter," while the plants of the new variety are decidedly a dwarf type which is compensated for by bearing relatively large flowers.

In addition to the foregoing characteristics, my new variety constitutes the first dwarf floribunda rose which bears flowers of carmine color in general color tonality, and the flowers are unique by virtue of exhibiting a ring of white color which extends above the aiglet into the petals and creates the effect of a white circle in the center of each flower.

The foregoing characteristics of my new variety definitely represent improvements over both parent varieties, and distinguish my new variety from all others of its class.

Asexual reproduction of the new variety by budding at Newark, New York, and also at Pleasanton, California, shows that the foregoing characteristics and distinctions come true to form and are established and transmitted through succeeding propagations.

The accompanying drawing shows typical specimens of the flowers, foliage and stems of my new variety in different stages of development and depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Chatter."
*Pollen parent.*—"Red Pinocchio."

Classification:
*Botanic.*—Large-flowered polyantha.
*Commercial.*—Floribunda.

FLOWER (Observations made from specimens grown in fields in Newark, New York, in the early part of the month of July and around mid-morning.)

Blooming habit: Recurrent—continuous.

Bud:
*Size.*—Medium; larger than "Chatter."
*Form.*—Ovoid; is not affected by wet or hot weather.
*Color.*—When sepals first divide—Victoria Lake, Plate 1. When petals begin to unfurl—Oxblood Red, Plate 1. When half blown: inside of petals—Carmine, Plate 1, lightly overcast with Spectrum Red, Plate 1; reverse of petals—Spectrum Red, Plate 1, lightly overcast with Carmine, Plate 1.
*Sepals.*—Branched ("hood" above bud); curl back when petals begin to unfurl. Color: inside—Light Lumiere Green, Plate 17; outside—Biscay Green, Plate 17.
*Calyx.*—Color—Biscay Green, Plate 17. Shape— pear. Size—small. Aspect—smooth. Odor when rubbed—none.
*Peduncle.* — Length — short. Aspect — smooth. Strength—erect; slender. Color—Absinthe Green, Plate 21.
*Opening.*—Opens up well; is not affected by adverse weather conditions.

Bloom:
*Size.*—Medium; average size when fully expanded 2½ inches.
*Borne.*—Sometimes singly and sometimes several together.
*Stems.*—Short; normal strength.
*Form.*—When first open—flat. Permanence—retains its form to the end.
*Petalage.*—Number of petals under normal conditions—20 to 25.
*Color.*—Center of flower—Carmine, Plate 1. Outer petals—Carmine, Plate 1, overcast with Pomegranate Purple, Plate 12. Base of petals (aiglet)—Primrose Yellow, Plate 30, with a small circle of White, Plate 53 above the aiglet. Inside of petals—Carmine, Plate 1, overcast with Spectrum Red, Plate 1. Reverse of petals—Carmine, Plate 1, lightly overcast with Rose Red, Plate 1; some petals on the reverse side have a mid-rib of Spinel Pink, Plate 26. General tonality from a distance—Carmine, Plate 1.
*Discoloration.*—General tonality at end of first day—Carmine, Plate 1. Second day—Carmine, Plate 1, lightly overcast with Spectrum Red, Plate 1. Third day—Carmine, Plate 1, lightly overcast with Rose Red, Plate 12.

Petals:
*Texture.*—Thick; is not affected by wet or hot weather.
*Appearance.*—Inside—velvety. Outside—satiny.
*Form.*—Oval; slightly notched.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long.

GENITAL ORGANS

Stamens, anthers: Medium size; many; regularly arranged around styles. Color—Antimony Yellow, Plate 15.
Stamens, filaments (threads): Short. Color—Picric Yellow, Plate 4.
Pollen: Color—Martius Yellow, Plate 4.
Styles: Columnar; uneven length; short; thin.
Stigmas: Color—Colonial Buff, Plate 30.
Ovaries: All enclosed in calyx.
Hips: None.
Seeds: None.

PLANT

Form: bush.
Growth: Vigorous; dwarf.
Foliage: 5 to 7 leaflets.
*Size.*—Medium.
*Quantity.*—Normal.
*Color.*—New foliage: upper side—Parrot Green, Plate 6, lightly overcast with Bordeaux, Plate 12; under side—Courge Green, Plate 17, overcast with Nopal Red, Plate 1. Old foliage: upper side—Dark Cress Green, Plate 31, overcast with Carmine, Plate 1; under side—Light Cress Green, Plate 31, lightly overcast with Carmine, Plate 1.
*Shape.*—Oval.
*Texture.*—Upper side—glossy. Under side—smooth.
*Ribs and veins.*—Ordinary.
*Edge.*—Serrated (saw-toothed).
*Serration.*—Single; small.
*Leaf stem.*—Color—Courge Green, Plate 17. Under side—prickles.
*Stipules.*—Short; smooth.

Wood:

*New wood.*—Color—Courge Green, Plate 17. Bark—smooth.

*Old wood.*—Color—Bice Green, Plate 17. Bark—smooth.

Thorns:

*Thorns.*—Quantity: on main stalks from base—ordinary; on laterals from stalk — ordinary. Form—narrow base; short; hooked downward. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its dwarf habit of growth, by the relatively large size of its buds and flowers which compensate for its dwarf habit of growth, by the distinctive carmine general color tonality which is unique in a dwarf floribunda rose, and by the distinctive ring of white color which extends above the aiglet into the petals of the flowers and gives the effect of a white circle in the center of each flower.

No references cited.